United States Patent
Orszulak

(10) Patent No.: US 8,353,904 B2
(45) Date of Patent: *Jan. 15, 2013

(54) ELECTROSURGICAL RADIO FREQUENCY ENERGY TRANSMISSION MEDIUM

(75) Inventor: James H. Orszulak, Nederland, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,935

(22) Filed: Jul. 11, 2011

(65) Prior Publication Data

US 2011/0264088 A1 Oct. 27, 2011

Related U.S. Application Data

(63) Continuation of application No. 12/889,720, filed on Sep. 24, 2010, now Pat. No. 7,985,220, and a continuation of application No. 11/523,888, filed on Sep. 20, 2006, now Pat. No. 7,819,865.

(51) Int. Cl.
*A61B 18/04* (2006.01)
(52) U.S. Cl. ............... 606/34; 606/51; 606/52; 606/32
(58) Field of Classification Search .............. 606/34, 606/37–42, 45–52; 174/110 R, 113 R, 113 C
See application file for complete search history.

(56) References Cited

U.S. PATENT DOCUMENTS

| | | | |
|---|---|---|---|
| 3,760,812 A | 9/1973 | Timm et al. | |
| 3,895,635 A | 7/1975 | Justus et al. | |
| 4,413,304 A | 11/1983 | Gerry | |
| 5,693,045 A | 12/1997 | Eggers | |
| 5,831,210 A | 11/1998 | Nugent | |
| 6,113,596 A | 9/2000 | Hooven et al. | |
| 6,190,385 B1 | 2/2001 | Tom et al. | |
| 6,300,573 B1 | 10/2001 | Horie et al. | |
| 6,394,949 B1 | 5/2002 | Crowley et al. | |
| 7,057,111 B2 | 6/2006 | Fung et al. | |
| 7,090,673 B2 | 8/2006 | Dycus et al. | |
| 7,147,638 B2 | 12/2006 | Chapman et al. | |

(Continued)

FOREIGN PATENT DOCUMENTS

EP 0061246 9/1982

(Continued)

OTHER PUBLICATIONS

International Search Report EP07018517.8 dated Dec. 17, 2007.
International search report EP09005095 dated Jun. 22, 2009.

*Primary Examiner* — Linda Dvorak
*Assistant Examiner* — Amanda Scott

(57) ABSTRACT

A system and method for transmitting electrosurgical energy from a generator to an electrosurgical instrument are provided. The electrosurgical system includes a generator adapted to generate electro surgical energy for treating tissue. The generator includes one or more active output terminals which supply energy to the tissue. The active output terminals are operatively connected to one or more supply lines. The generator also includes one or more return output terminal which returns energy from the tissue. The return output terminals are operatively connected to at least one return line. The system also includes an electrosurgical instrument operatively connected to the one or more supply lines and one or more return electrodes operatively connected to one or more return lines. The system further includes an electrosurgical cable including one or more supply lines and one or more return lines. The one or more supply lines and one or more return lines are wound in a double helix fashion such that the electrical field along the cable is mitigated along the length thereof.

19 Claims, 6 Drawing Sheets

| U.S. PATENT DOCUMENTS | | | | FOREIGN PATENT DOCUMENTS | | |
|---|---|---|---|---|---|---|
| 7,819,865 B2 | 10/2010 | Orszulak | | EP | 01619124 | 10/1994 |
| 2003/0229344 A1 | 12/2003 | Dycus et al. | | EP | 0750886 | 1/1997 |
| 2004/0254573 A1 | 12/2004 | Dycus et al. | | GB | 2321193 | 7/1998 |
| 2005/0049454 A1 | 3/2005 | Ouchi | | GB | 2326519 | 12/1998 |
| 2006/0148306 A1 | 7/2006 | Desinger et al. | | WO | 2006048199 | 5/2006 |
| 2008/0027504 A1 | 1/2008 | Bedenbaugh | | WO | 2006081191 | 8/2006 |

ELECTROSURGICAL RADIO FREQUENCY ENERGY TRANSMISSION MEDIUM

CROSS REFERENCE TO RELATED APPLICATIONS

This application is a continuation of U.S. patent application Ser. No. 12/889,720, filed on Sep. 24, 2010, which is a continuation of U.S. patent application Ser. No. 11/523,888, filed on Sep. 20, 2006, now U.S. Pat. No. 7,819,865, the entire contents of each of which are incorporated by reference herein.

BACKGROUND

1. Technical Field

The present disclosure relates to an electrosurgical system and method for performing electrosurgical procedures. More particularly, the present disclosure relates to a system and method for effectively transmitting electrosurgical radio frequency energy from an electrosurgical generator to a treatment site with reduced energy loss.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

Transmission of electrosurgical energy to the treatment site, namely from the electrosurgical generator to the instrument, is accomplished via an electrosurgical cable. During transmission an electrical field is generated through the cable and stray electrosurgical RF energy is typically emitted along the cable path, which tends to reduce treatment energy. Moreover, the electrical fields may interfere with the operation of other electronic equipment in the surgical arena, such as patient monitoring equipment.

SUMMARY

The present disclosure relates to transmission of electrosurgical radio frequency ("RF") energy. An electrosurgical cable is disclosed having close proximity electrical field coupling between a supply and return transmission lines. The coupling maximizes application of the RF energy delivered during surgery and minimizes the stray RF energy radiated by the supply and return leads. Close proximity electrical field coupling significantly reduces the electrical field via field cancellation thereby increasing patient and surgeon safety. Coupling provides a low loss inductive/capacitive ("LC") transmission medium via a three-dimensional geometric orientation of the supply and return leads. The geometric orientation affects LC reactive components and reduces uncontrolled capacitive reactance caused by stray RF radiation. In particular, capacitive reactance is caused by antenna effect (e.g., rapid discharge of stray RF energy) for transmission mediums shorter than half a wavelength. Therefore, loss of stray RF energy is contained to a predetermined level which also reduces capacitive loading to the energy source (e.g., electrosurgical energy).

According to one aspect of the present disclosure a system for transmitting electrosurgical energy from a generator to an electrosurgical instrument is disclosed. The electrosurgical system includes a generator adapted to generate electrosurgical energy for treating tissue. The generator includes one or more active output terminals which supply energy to the tissue. The active output terminals are operatively connected to one or more supply lines. The generator also includes one or more return output terminal which returns energy from the tissue. The return output terminals are operatively connected to at least one return line. The system also includes an electrosurgical instrument operatively connected to the one or more supply lines and one or more return electrodes operatively connected to one or more return lines. The system further includes an electrosurgical cable including one or more supply lines and one or more return lines. The one or more supply lines and one or more return lines are wound in a double helix fashion such that the electrical field along the cable is mitigated along the length thereof.

According to another aspect of the present disclosure an electrosurgical cable is disclosed. The cable is configured to transmit electrosurgical energy from a source of electrosurgical energy to an electro surgical instrument. The source of electrosurgical energy includes one or more active output terminals and one or more return output terminals. The electrosurgical cable includes one or more supply lines operatively connected to the active output terminals and one or more return lines operatively connected to the return output terminals. The one or more supply lines and the one or more return lines are wound in the double helix comprising geometrically of two congruent helixes having a same axis, differing by a translation along the axis such that the electrical field along the cable is mitigated along the length thereof.

According to a further aspect of the present disclosure a method for transmitting high frequency electrosurgical to an electrosurgical instrument is disclosed. The method includes the step of providing a generator adapted to generate electro surgical energy for treating tissue. The generator includes one or more active output terminals which supply energy to the tissue. The active output terminals are operatively connected to one or more supply lines. An electrosurgical instrument is operatively connected to the at least one supply line. The generator also includes one or more return output terminal which returns energy from the tissue. The return output terminals are operatively connected to at least one return line. One or more return electrodes are operatively connected to one or more return lines. The method also includes the step of enclosing the one or more supply lines and one or more return lines within an electro surgical cable. The supply lines and the return lines are wound in a double helix fashion such that the electrical field along the cable is mitigated along the length thereof.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems and either an endoscopic instrument or an open instrument. It should also be appreciated that different electrical and mechanical connections and other considerations apply to each particular type of instrument.

The present disclosure provides for an electrosurgical transmission cable wound in a double helix having a proximal geometric relationship in three-dimensional physical space, to control the inductive and capacitive components of the transmission cable and significantly reduce the capacitive leakage due to RF radiation. The transmission cable according to present disclosure being wound in a double helix minimizes the stray RF radiation by reducing the transmitting antenna effect for transmission mediums shorter than ½ wavelength.

Figure 1:
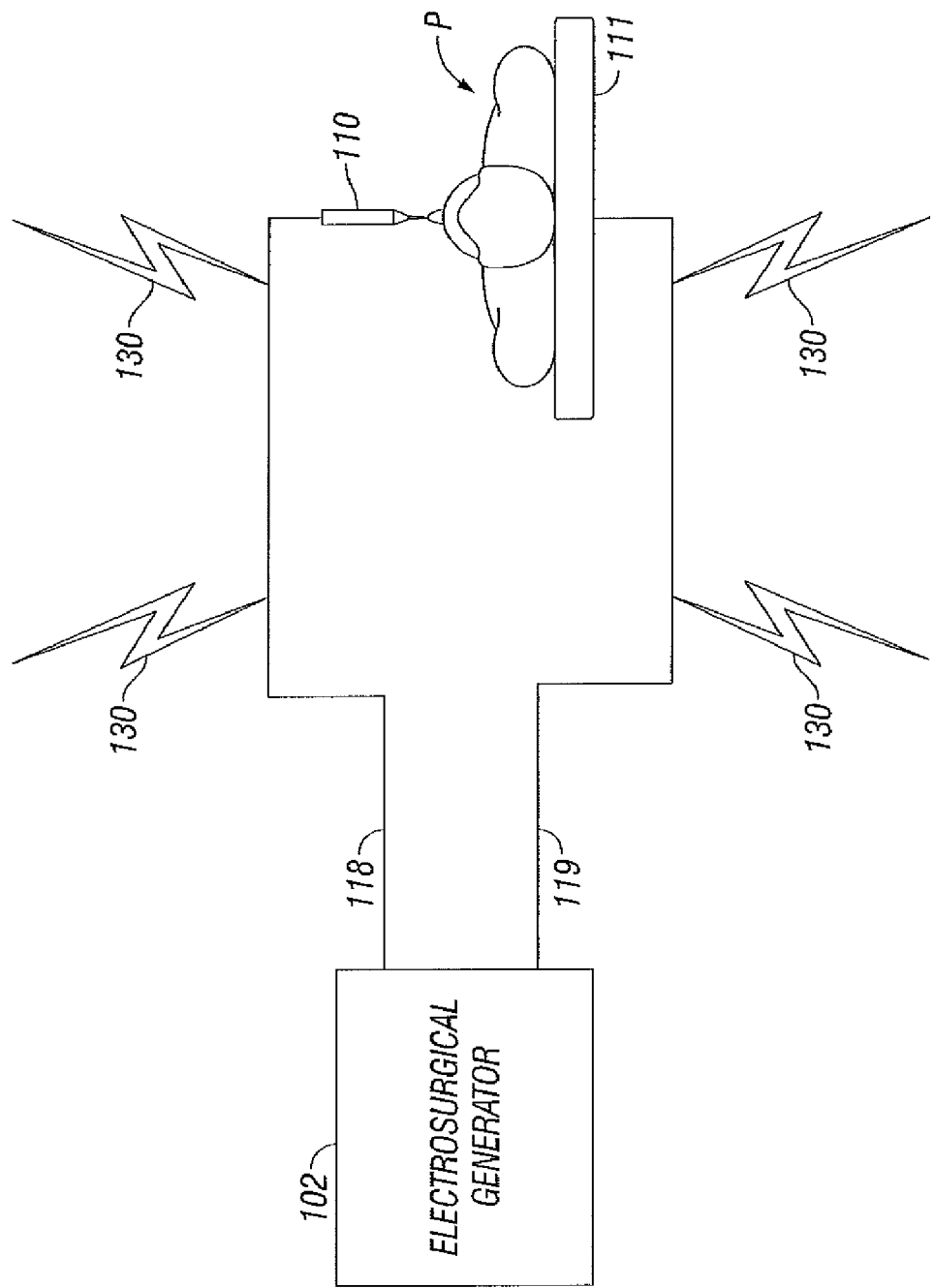
FIG. 1 is a schematic block diagram of a prior art electrosurgical system.

FIG. 1 is a schematic illustration of a prior art electrosurgical system. The system includes an electrosurgical generator 102 supplying electrosurgical radio frequency ("RF") energy to a monopolar electrosurgical instrument 110 via a supply transmission line 118. The RF energy is returned to the generator 102 through a return electrode 111, shown as a return pad via a return transmission line 119. Conventionally, the supply and return lines 118, 119 are oriented in a random fashion and are not oriented with respect to each other to minimize stray RF energy emitted shown as lines 130, which occurs as RF energy flows therethrough. Random placement of the supply and return lines 118, 119 results in uncontrolled capacitive coupling due to stray RF radiation. Radiating RF energy source causes a transmitting antenna effect caused by random orientation of the supply and return lines 118, 119 during surgical procedures and forms an alternate RF leakage path to the desired RF treatment energy.

Figure 2:
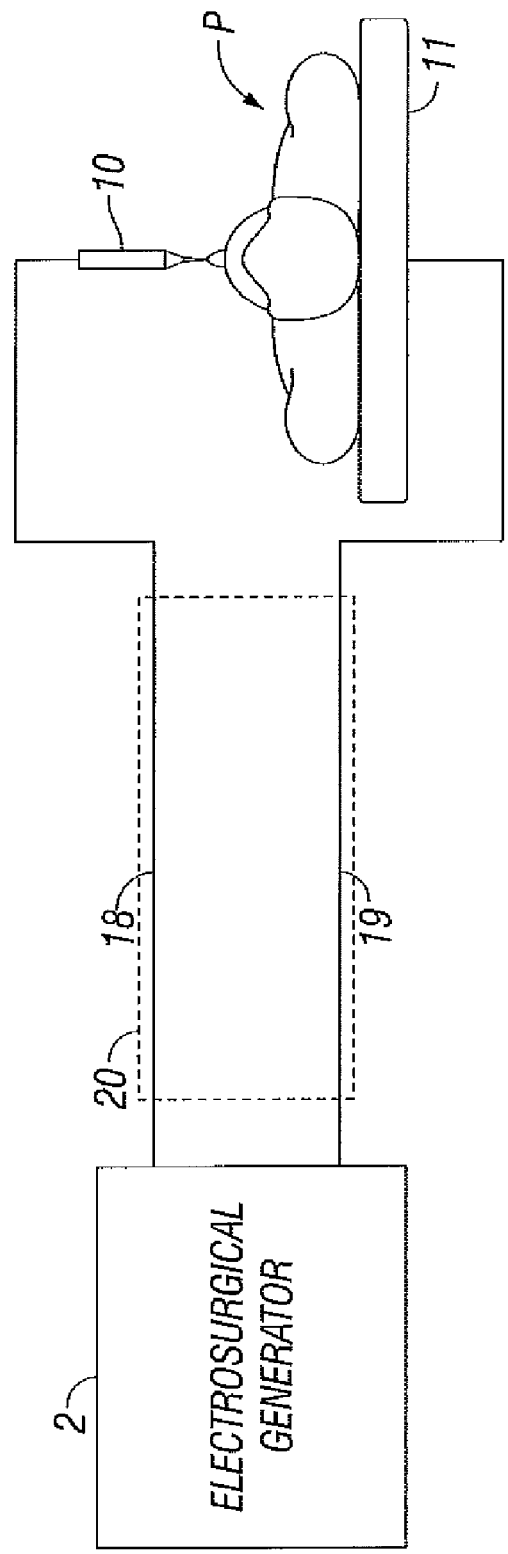
FIG. 2 is a schematic block diagram of one embodiment of an electrosurgical system according to the present disclosure.

FIG. 2 is a schematic illustration of an electrosurgical system according to the present disclosure. The system is a monopolar electrosurgical system that includes an electrosurgical instrument 10 having one or more electrodes for treating tissue of a patient P. Electrosurgical RF energy is supplied to the instrument 10 by a generator 2 via a supply line 18, which is operatively connected to an active output terminal, allowing the instrument 10 to coagulate, seal and/or otherwise treat tissue. Energy is returned to the generator 2 through a return electrode 11 and transmitted through a return line 19, which is operatively connected to a return output terminal. The supply and return lines 18, 19 are enclosed within a cable 20.

System may include a plurality of return electrodes 11, which is believed to minimize the chances of damaged tissue by maximizing the overall contact area with the patient P. In addition, the generator 2 and the return electrode 11 may be configured for monitoring so called "tissue-to-patient" contact to insure that sufficient contact exists therebetween to further minimize chances of tissue damage. The generator 2 may include a plurality of supply and return terminals and corresponding number of transmission cables (e.g., two of each).

Figure 3:
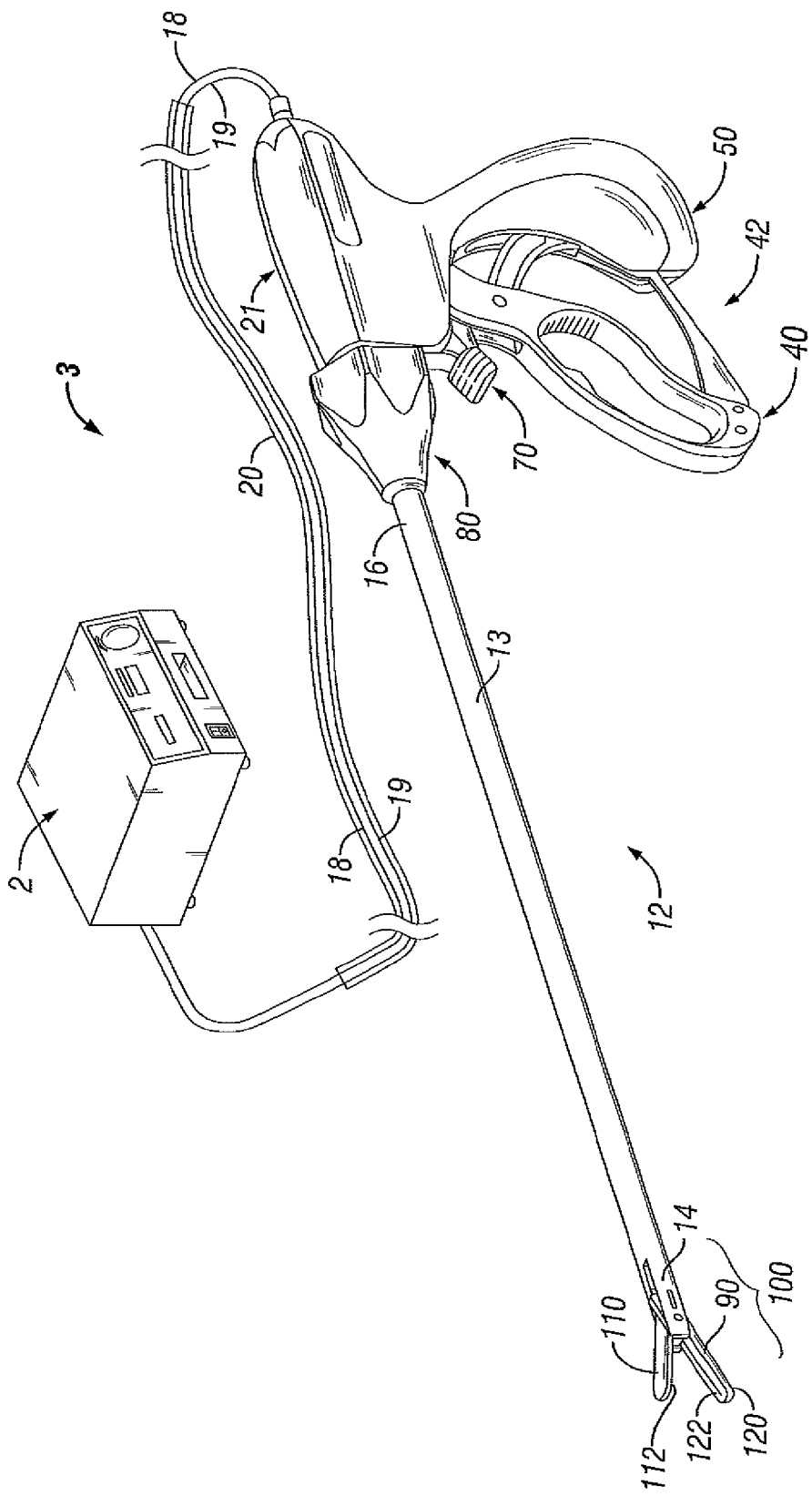
FIG. 3 is a perspective view of another embodiment of an electrosurgical system according to one embodiment of the present disclosure.

FIG. 3 shows an electrosurgical system 3 according to the present disclosure. The system 3 is a bipolar electrosurgical system that includes an electrosurgical forceps 12 having opposing jaw members. The forceps 12 includes one or more shaft members 13 having an end effector assembly 100 disposed at the distal end. The end effector assembly 100 includes two jaw members 110, 120 movable from a first position wherein the jaw members are spaced relative to on another to a closed position wherein the jaw members 110 and 120 cooperate to grasp tissue therebetween. Each of the jaw members includes an electrically conductive sealing plate connected to an energy source (e.g., a generator 2) that communicates electrosurgical energy through the tissue held therebetween. Electrosurgical RF energy is supplied to the forceps 12 by generator 2 via the supply line 18 operatively connected to the active electrode and returned through the return line 19 operatively connected to the return electrode. The supply and return lines 18, 19 are enclosed within cable 20.

As shown in FIG. 3, the forceps 12 is an endoscopic vessel sealing bipolar forceps. The forceps 12 is configured to support the effector assembly 100. Those skilled in the art will understand that the invention according to the present disclosure may be adapted for use with either an endoscopic instrument or an open instrument. More particularly, forceps 12 generally includes a housing 21, a handle assembly 42, a rotating assembly 80, and a trigger assembly 70, which mutually cooperate with the end effector assembly 100 to grasp and treat tissue. The forceps 12 also includes a shaft 13, which has a distal end 14 that mechanically engages the end effector assembly 100 and a proximal end 16 that mechanically engages the housing 21 proximate the rotating assembly 80. Handle assembly 42 includes a fixed handle 50 and a movable handle 40. Handle 40 moves relative to the fixed handle 50 to actuate the end effector assembly 100 and enable a user to grasp and manipulate tissue as shown in FIG. 3.

Figure 4:
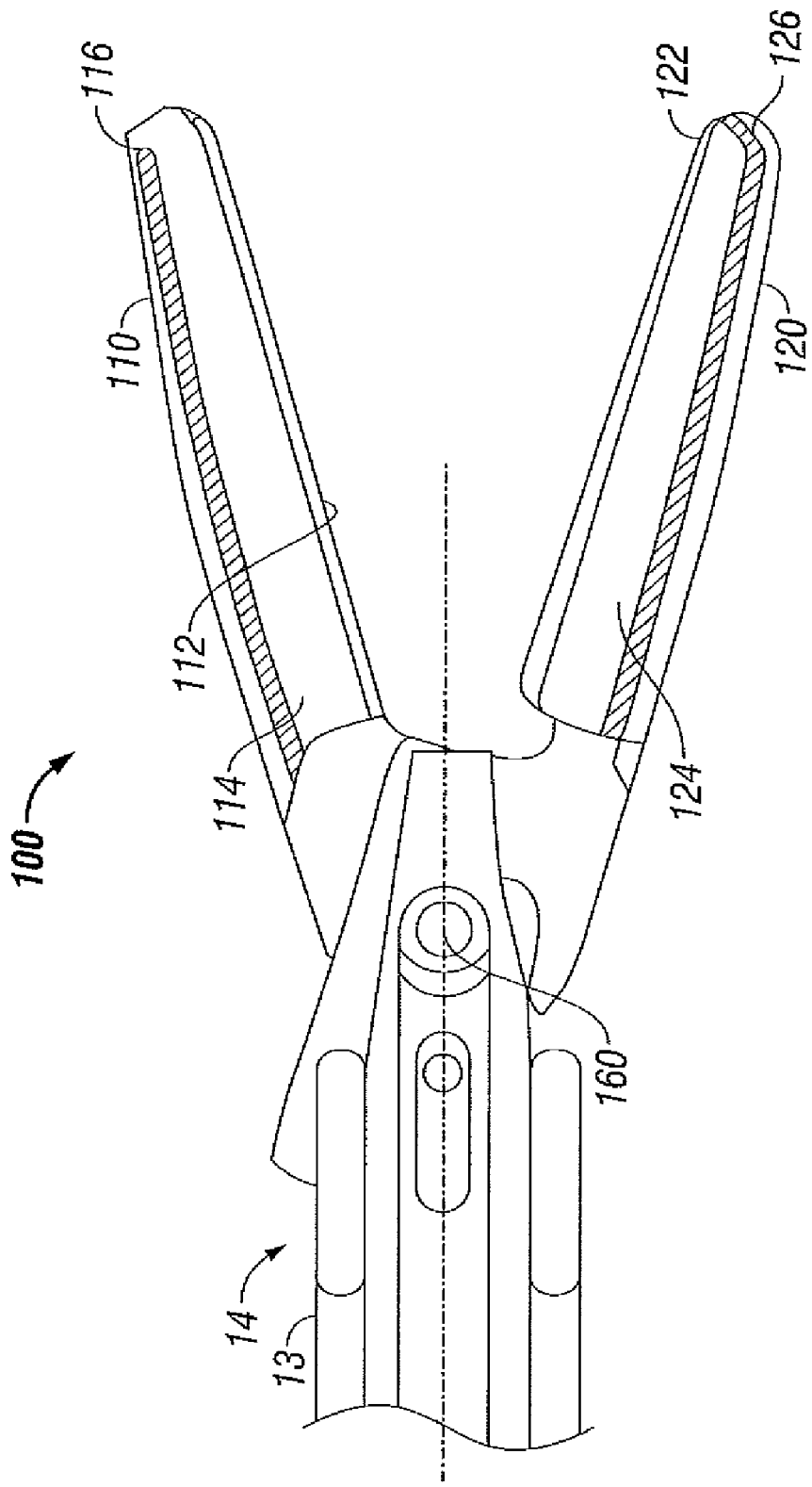
FIG. 4 is a side, partial internal view of an endoscopic forceps according to the present disclosure.

Referring to FIGS. 3 and 4, the end effector assembly 100 includes opposing jaw members 110 and 120 having electrically conductive sealing plate 112 and 122, respectively, attached thereto for conducting electrosurgical energy through tissue. More particularly, the jaw members 110 and 120 move in response to movement of the handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto. Further details relating to one envisioned endoscopic forceps is disclosed in commonly-owned U.S. application Ser. No. 10/474,169 entitled "VESSEL SEALER AND DIVIDER."

The jaw members 110 and 120 are activated using a drive assembly (not shown) enclosed within the housing 21. The drive assembly cooperates with the movable handle 40 to impart movement of the jaw members 110 and 120 from the open position to the clamping or closed position. Examples of a handle assemblies are shown and described in the above identified application as well as commonly-owned U.S. application Ser. No. 10/369,894 entitled "VESSEL SEALER AND DIVIDER AND METHOD MANUFACTURING SAME" and commonly owned U.S. application Ser. No.

10/460,926 entitled "VESSEL SEALER AND DIVIDER FOR USE WITH SMALL TROCARS AND CANNULAS."

Jaw members 110 and 120 also include insulators 116 and 126, which together with the outer, non-conductive plates of the jaw members 110 and 120 are configured to limit and/or reduce many of the known undesirable effects related to tissue sealing, e.g., flashover, thermal spread and stray current dissipation.

In addition, the handle assembly 42 of this particular disclosure includes a four-bar mechanical linkage that provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. The details relating to the inter-cooperative relationships of the inner working components of forceps 12 are disclosed in the above-cited commonly-owned U.S. patent application Ser. No. 10/369,894. Another example of an endoscopic handle assembly which discloses an off-axis, lever-like handle assembly, is disclosed in the above-cited U.S. patent application Ser. No. 10/460,926.

The forceps 12 also includes a rotating assembly 80 mechanically associated with the shaft 13 and the drive assembly (not shown). Movement of the rotating assembly 80 imparts similar rotational movement to the shaft 13 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 3 and 4, the end effector assembly 100 attaches to the distal end 14 of shaft 13. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

The forceps 12 may be designed such that it is fully or partially disposable depending upon a particular purpose or to achieve a particular result. For example, end effector assembly 100 may be selectively and releasably engageable with the distal end 14 of the shaft 13 and/or the proximal end 16 of the shaft 13 may be selectively and releasably engageable with the housing 21 and handle assembly 42. In either of these two instances, the forceps 12 may be either partially disposable or reposable, such as where a new or different end effector assembly 100 or end effector assembly 100 and shaft 13 are used to selectively replace the old end effector assembly 100 as needed.

Figure 5:
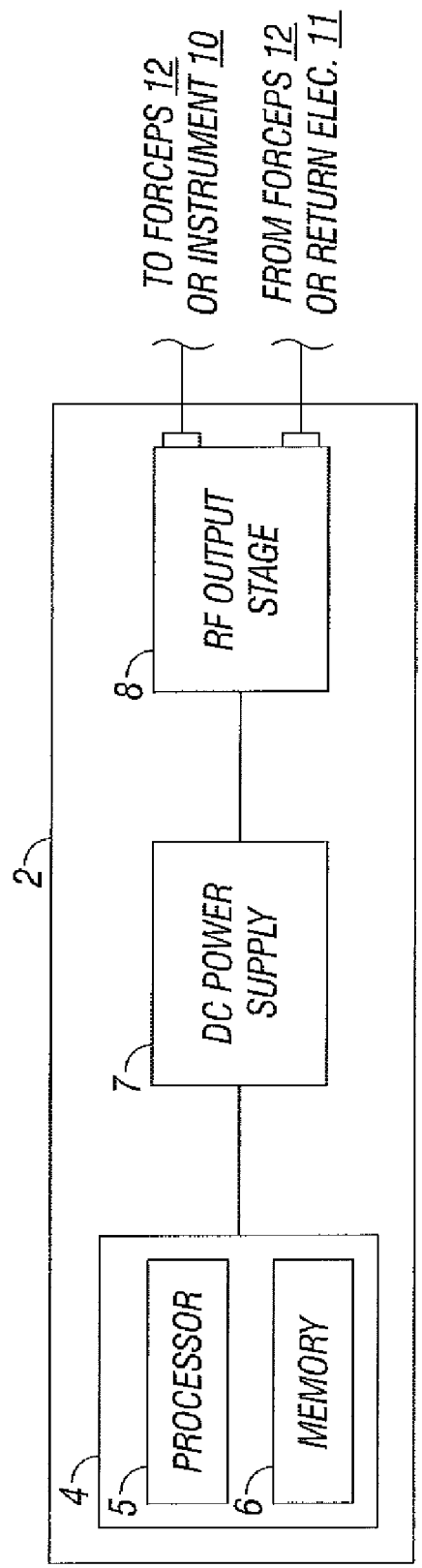
FIG. 5 is a schematic block diagram of a generator according to the present disclosure.

With reference to FIGS. 2, 3 and 5, the generator 2 includes suitable input controls (e.g., buttons, activators, switches, touch screen, etc.) for controlling the generator 2. In addition, the generator 2 may include one or more suitable display screens for providing the surgeon with variety of output information (e.g., intensity settings, treatment complete indicators, etc.). The controls allow the surgeon to adjust power of the RF energy, waveform, and other suitable parameters to achieve the desired waveform suitable for a particular task (e.g., coagulating, tissue sealing, intensity setting, etc.). The instrument 10 and/or forceps 12 may also include a plurality of input controls that may be redundant with certain input controls of the generator 2. Placing the input controls at the instrument 10 and/or forceps 12 allows for easier and faster modification of RF energy parameters during the surgical procedure without requiring interaction with the generator 2.

FIG. 5 shows a schematic block diagram of the generator 2 having a controller 4, a high voltage DC power supply 7 ("HVPS") and an RF output stage 8. The DC power supply 7 provides DC power to the RF output stage 8, which then converts DC power into RF energy and delivers the RF energy to the instrument 10 or forceps 12. The controller 4 includes a microprocessor 5 operatively connected to a memory 6 which may be volatile type memory (e.g., RAM) and/or non-volatile type memory (e.g., flash media, disk media, etc.). The microprocessor 5 includes an output port that is operatively connected to the HVPS 7 and/or RF output stage 8 allowing the microprocessor 5 to control the output of the generator 2 according to either open and/or closed control loop schemes. A closed loop control scheme may be a feedback control loop wherein the sensor circuitry 11, which may include a plurality of sensing mechanisms (e.g., tissue impedance, tissue temperature, output current and/or voltage, etc.), provides feedback to the controller 4. The controller 4 then signals the HVPS 7 and/or RF output stage 8, which then adjusts DC and/or RF power supply, respectively. The controller 4 also receives input signals from the input controls of the generator 2 and/or instrument 10. The controller 4 utilizes the input signals to adjust power outputted by the generator 2 and/or performs other suitable control functions thereon.

Figure 6:
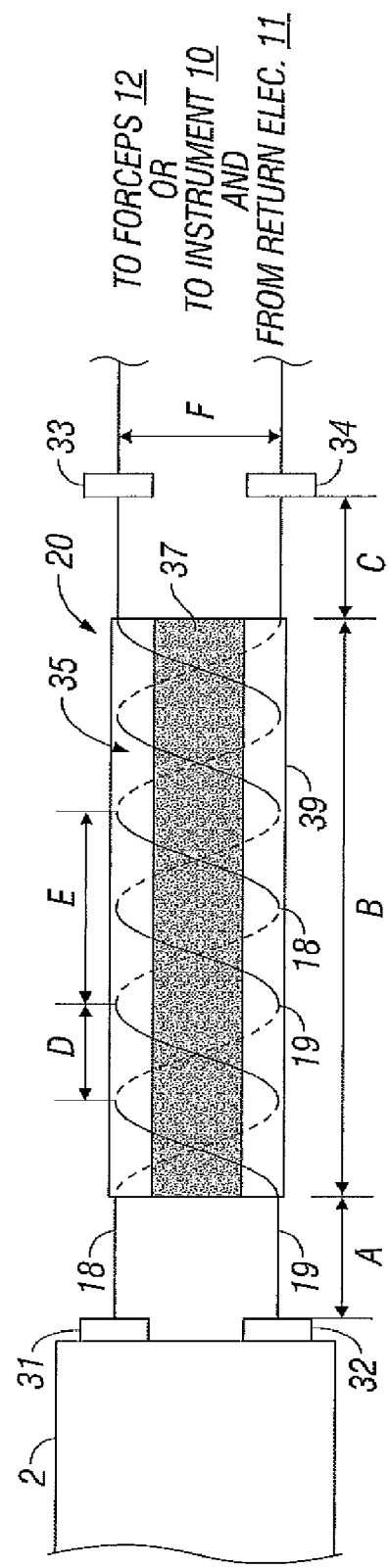
FIG. 6 is a cross-sectional view of an electrosurgical cable according to the present disclosure.

FIG. 6 shows a cross-sectional view of the cable 20. The cable 20 includes the supply and return lines 18, 19. The supply and return lines 18, 19 are operatively connected to the generator 2 via connectors 31, 32 respectively. Connectors 31, 32 may be either of fixed or detachable type allowing for the usage of multiple instruments and return electrode pads with the generator 2. The generator 2 and the connectors 31, 32 may also include identification means (e.g., bar codes or other codes disposed on the connectors and scanners operatively connected to the generator, etc.) that identify the device operatively connected to the connectors 31, 32. Upon connection of the connectors 31, 32, the generator 2 identifies the instrument and performs particular preprogrammed operations (e.g., initialize procedure, set operating parameters, adjust power settings, etc.).

The supply and return lines 18, 19 may be insulated. Various types of insulating materials may be used, which are within the purview of those skilled in the art. The supply and return lines 18, 19 extend from the connectors 31, 32 respectively for a distance A, which is optimally controlled by the location of connectors 31, 32 and is between from about 0.1 inches to about 6 inches. The lines 18, 19 are then helix wound in a wound portion 35, which be about 7 feet or more depending upon a desired cable inductance and capacitance. Alternatively, the wound portion 35 may extend from the connectors 31, 32 without extending the supply and return lines 18, 19 for the distance A.

The wound portion 35, along cable length B, can be of any length depending on geometric configuration and physical properties (e.g., tensile strength, flexibility, etc.) of materials used in manufacturing of cable components. More specifically the lines 18, 19 are oriented in a double helix which includes two congruent helixes with the same axis, differing by a translation along the axis. The lines 18, 19 may be oriented in a plurality of other arrangements which wrap the lines 18, 19 around themselves. The arrangement of the lines 18, 19 in a double helix orients the opposing electrical fields generated by the electrosurgical RF energy passing therethrough to mitigate and/or cancel out thereby minimizing the amount of lost stray electrical RF energy.

The lines 18, 19 are wound within the cable 20 around a dielectric insulator 37, which provides support for the lines 18, 19, an insulative sheath 39 covers the lines 18, 19. The insulator 37 and the sheath 39 may be of the same type. The lines 18, 19 may comprise wire that has an inductance rating at 473 kHz of 7.37 µH and A, capacitance at 1 MHz of 32.0 PF to yield a cable self resonance of 10.4 MHz. The wire may be 26 gauge and 15 kV rated.

With reference to FIG. 6 and the portion 35, the distance D, which represents the distance between one apex of one helix and a nearest apex of another helix, may be about ½ inch. The distance E, which is the distance between two apexes of the same helix may be about 1 inch. The outer diameter F of the cable 20 may be about ⅜ of an inch.

Cable 20 as illustrated in FIG. 6, provides a transmission medium to deliver RF energy from the generator 20 to a tissue site. The cable 20 represents one example of a preferred embodiment for the RF transmission medium, which reduces the radiated RF electrical field and maximizes the applied clinical treatment energy delivered to the tissue site. The dimensions A, B, C, D, E and F of FIG. 6 form a unique proximal geometric relationship in three dimensional space to control the electrical field coupling between the active and return output terminals of the generator 20 to significantly reduce the Volts per meter electrical field radiation by field cancellation.

The physical dimensions A, B, C, D, E and F are interdependent and optimized to provide a low loss inductive and capacitive transmission medium, which in addition to controlling the electrical field, reduces uncontrolled capacitive coupling caused by stray RF radiation. In particular the following equations (1) and (2) illustrate the interdependent relationship of dimensions A, B, C, D, E and F with respect to inductive and capacitive properties of the cable 20.

$$\text{Inductance} = B(10.16 \times 10^{-9}) Ln[(2 \times D)/d)] + 2(A+C) \quad (\mu H/\text{in. for specified wire}) \quad (1)$$

$$\text{Capacitance} = [(B \times (0.7065 \times 10^{-12}))/Ln[(2 \times D)/d]]er \quad (2)$$

In equations (1) and (2) d denotes diameter of the wire (e.g., supply and return lines 18, 19), er denotes the dielectric constant of the wire insulator. Further, E=2×D, the ratio of E to D allows to establish a continuum of the helix configuration and F=k×D, where k is a constant from about 0.5 to about 1.5.

At the distal end of the portion 35, the lines 18, 19 are unwound and are operatively connected to device connectors 33, 34 respectively. The lines 18, 19 extend a distance C from the portion 35 to the connectors 33, 34 in an unwound state for approximately 2.5 feet. The initial length A of the lines and the unwound state length C are maintained relatively consistent with varying lengths of wire with length of the wound portion 35 varying for different overall lengths.

In bipolar surgery, the connectors 33, 34 may be situated on the forceps 12. In monopolar surgery, the connector 33 is operatively connected to the instrument 10 and the connector 34 is connected to the return electrode 11. As discussed above, in situations where a plurality of return electrodes are used, the return line 19 may split into corresponding number of leads to operatively connect all of the return electrodes 11 to the generator 2. With monopolar surgery the length C for line 18 may lengthen greater than 2.5 feet with a corresponding decrease in line 19 to accommodate manipulation of surgical instrument in the operating site.

The cable 20 according to the present disclosure orients the supply and return lines 18, 19 so that the electrical fields generated therethrough are canceled, thereby reducing the amount of leaked stray RF energy. More specifically, placement and orientation of the lines 18, 19 in the manner discussed above provides for close proximity of electrical fields generated during transmission of electrosurgical RF energy and maximizes amount of energy delivered to the treatment site. Reducing the electrical fields also increases safety of personnel and the patient.

Reduced RF radiation decreases capacitive and RF field leakage and improves RF control of the delivered energy. Reduced RF radiation also decreases RF transmission loss and improves efficiency of the generator 2 by reducing RF harmonic component, minimizing corruption of the RF source and reducing peripheral conductive and radiative emissions. Further, reducing RF radiation also decreases the RF noise to additional equipment found in the room, such as patient monitoring equipment.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
a generator adapted to generate electrosurgical energy for treating tissue, the generator including at least one active output terminal that supplies energy to the tissue, the at least one active output terminal operatively connected to at least one supply line, the generator also including at least one return output terminal that returns energy from the tissue, the at least one return output terminal operatively connected to at least one return line;
an electrosurgical instrument operatively connected to the at least one supply line;
at least one return electrode operatively connected to the at least one return line; and
an electro surgical cable including the at least one supply line and the at least one return line, at least a portion of the at least one supply line and at least a portion of the at least one return line being wound in a double helix having a first helix and a second helix, wherein at least two parameters of the electrosurgical cable, including a length of the double helix and an apex distance between an apex of the first helix and a nearest apex of the second helix, are optimized to achieve desired inductive and capacitive properties of the electrosurgical cable.

2. The electrosurgical system of claim 1, wherein the at least two parameters of the electrosurgical cable further include one or more of the parameters selected from the group consisting of a distance between two apexes of the same helix and an outer diameter of the cable.

3. The electrosurgical system of claim 1, wherein the at least two parameters of the electrosurgical cable further include one or more of the parameters selected from the group consisting of (a) a distance between a first end of the wound portion of the cable and the output terminals of the generator, and (b) a distance between a second end of the wound portion of the cable and at least one connector of the electrosurgical instrument.

4. The electrosurgical system of claim 1, wherein the apex distance between the apex of the first helix and the nearest apex of the second helix is about half a distance between two apexes of the same helix and the first and second helixes are disposed a predetermined distance apart as a function of the apex distance.

5. The electrosurgical system of claim 1, wherein the double helix includes two congruent helixes having a same axis and separated a predetermined distance from each other along the axis.

6. The electrosurgical system of claim 1, wherein the at least one supply line and the at least one return line are covered by a sheath.

7. The electrosurgical system of claim 1, wherein the at least one supply line and the at least one return line are wound around a dielectric insulator.

8. An electrosurgical system of claim 1, wherein the electrosurgical instrument is an electrosurgical forceps including at least one shaft member having an end effector assembly disposed at a distal end thereof, the end effector assembly including two jaw members movable from a first position in spaced relation relative to one another to at least one subsequent position wherein the jaw members cooperate to grasp tissue therebetween, each of the jaw members including an electrical sealing plate, wherein one electrical sealing plate is operatively connected to the at least one supply line and another electrical sealing plate is operatively connected to the at least one return line.

9. An electrosurgical cable configured to transmit electrosurgical energy from a source of electrosurgical energy to an electrosurgical instrument, the source of electro surgical energy having at least one active output terminal and at least one return output terminal, the electrosurgical cable comprising:
at least one supply line operatively connected to the at least one active output terminal and at least one return line operatively connected to the at least one return output terminal, wherein at least a portion of the at least one supply line and at least a portion of the at least one return line are wound in a double helix having a first helix and a second helix, wherein at least two parameters of the electrosurgical cable, including a length of the double helix and an apex distance between an apex of the first helix and a nearest apex of the second helix, are optimized to achieve desired inductive and capacitive properties of the electrosurgical cable.

10. The electrosurgical cable of claim 9, wherein the apex distance between the apex of the first helix and the nearest apex of the second helix are about half a distance between two apexes of the same helix, wherein the first and second helixes are disposed a predetermined distance apart as a function of the apex distance.

11. The electrosurgical cable of claim 9, wherein the double helix includes two congruent helixes having a same axis and separated a predetermined distance from each other along the axis.

12. The electrosurgical cable of claim 9, wherein the electrosurgical instrument is a monopolar electro surgical instrument operatively connected to the at least one supply line, and wherein at least one return electrode is operatively connected to the at least one return line.

13. The electrosurgical cable of claim 9, wherein the electrosurgical instrument is an electrosurgical forceps comprising at least one shaft member having an end effector assembly disposed at a distal end thereof, the end effector assembly including two jaw members movable from a first position in spaced relation relative to one another to at least one subsequent position wherein the jaw members cooperate to grasp tissue therebetween, each of the jaw members including an electrical sealing plate, wherein one electrical sealing plate is operatively connected to the at least one supply line and another electrical sealing plate is operatively connected to the at least one return line.

14. The electrosurgical cable of claim 9, wherein the at least one supply line and the at least one return line are wound around a dielectric insulator.

15. A method for transmitting high frequency electrosurgical energy to an electrosurgical instrument, the method comprising:
providing a generator adapted to generate electrosurgical energy for treating tissue, the generator including at least one active output terminal that supplies energy to the tissue, the at least one active output terminal operatively connected to at least one supply line, wherein an electrosurgical instrument is operatively connected to the at least one supply line, the generator also including at least one return output terminal that returns energy from the tissue, the at least one return output terminal operatively connected to at least one return line, wherein at least one return electrode is operatively connected to the at least one return line;
enclosing the at least one supply line and the at least one return line within an electrosurgical cable, at least a portion of the at least one supply line and at least a portion of the at least one return line being wound in a double helix having a first helix and a second helix; and
optimizing at least two parameters of the electrosurgical cable, including a length of the double helix and an apex distance between an apex of the first helix and a nearest apex of the second helix, to achieve desired inductive and capacitive properties of the electrosurgical cable.

16. The method of claim 15, wherein the apex distance between the apex of the first helix and the nearest apex of the second helix is about half a distance between two apexes of the same helix and the first and second helixes are disposed a predetermined distance apart as a function of the apex distance.

17. The method of claim 15, wherein the electrosurgical instrument is a monopolar electrosurgical instrument operatively connected to the at least one supply line, and wherein the at least one return electrode is operatively connected to the at least one return line.

18. The method of claim 15, further comprising the step of:
providing an electrosurgical forceps comprising at least one shaft member having an end effector assembly disposed at a distal end thereof, the end effector assembly including two jaw members movable from a first position in spaced relation relative to one another to at least one subsequent position wherein the jaw members cooperate to grasp tissue therebetween, each of the jaw members including an electrical sealing plate, wherein one electrical sealing plate is operatively connected to the at least one supply line and another electrical sealing plate is operatively connected to the at least one return line.

19. The method of claim 15, wherein the at least one supply line and the at least one return line are wound around a dielectric insulator.

* * * * *